(12) United States Patent
Gertner et al.

(10) Patent No.: US 7,776,379 B2
(45) Date of Patent: Aug. 17, 2010

(54) METALLIC STRUCTURES INCORPORATING BIOACTIVE MATERIALS AND METHODS FOR CREATING THE SAME

(75) Inventors: Michael E. Gertner, Menlo Park, CA (US); Nazila Dadvand, Montreal (CA); Richard L. Klein, Santa Rosa, CA (US); Nathan Christopher Maier, Forestville, CA (US)

(73) Assignee: Medlogics Device Corporation, Santa Rosa, CA (US)

( * ) Notice: Subject to any disclaimer, the term of this patent is extended or adjusted under 35 U.S.C. 154(b) by 1343 days.

(21) Appl. No.: 11/203,083

(22) Filed: Aug. 12, 2005

(65) Prior Publication Data

US 2006/0062820 A1   Mar. 23, 2006

Related U.S. Application Data

(63) Continuation-in-part of application No. 10/497,198, filed on Dec. 13, 2004, now abandoned, which is a continuation-in-part of application No. 10/196,296, filed as application No. PCT/US02/38275 on Nov. 27, 2002.

(60) Provisional application No. 60/323,071, filed on Sep. 19, 2001, provisional application No. 60/333,523, filed on Nov. 28, 2001, provisional application No. 60/364,083, filed on Mar. 15, 2002.

(51) Int. Cl.
*A61L 33/00* (2006.01)
*B05D 5/00* (2006.01)
*B05D 1/36* (2006.01)
*A61F 2/06* (2006.01)

(52) U.S. Cl. ............. 427/2.1; 427/2.24; 427/2.25; 427/256; 427/261; 427/282; 623/1.39; 623/1.42; 623/1.43; 623/1.46

(58) Field of Classification Search ............... 427/256, 427/259, 261, 282, 2.1–2.31
See application file for complete search history.

(56) References Cited

U.S. PATENT DOCUMENTS

| | | |
|---|---|---|
| 3,936,577 A | 2/1976 | Christini et al. |
| 4,358,922 A | 11/1982 | Feldstein |
| 4,374,669 A | 2/1983 | MacGregor |
| 4,397,812 A | 8/1983 | Mallory, Jr. |
| 4,547,407 A | 10/1985 | Spencer, Jr. |
| 4,729,871 A | 3/1988 | Morimoto |
| 4,917,895 A | 4/1990 | Lee et al. |
| 5,145,517 A | 9/1992 | Feldstein et al. |
| 5,464,650 A | 11/1995 | Berg et al. |
| 5,545,208 A | 8/1996 | Wolff et al. |
| 5,725,570 A | 3/1998 | Heath |
| 5,725,572 A | 3/1998 | Lam et al. |
| 5,772,864 A | 6/1998 | Moller et al. |
| 5,837,313 A | 11/1998 | Ding et al. |
| 5,843,172 A | 12/1998 | Yan |
| 5,873,904 A | 2/1999 | Ragheb et al. |
| 5,958,430 A | 9/1999 | Campbell et al. |
| 5,972,027 A | 10/1999 | Johnson |
| 5,976,169 A | 11/1999 | Imran |
| 6,019,784 A | 2/2000 | Hines |
| 6,054,111 A | 4/2000 | Antonietti et al. |
| 6,120,536 A | 9/2000 | Ding et al. |
| 6,123,861 A | 9/2000 | Santini, Jr. et al. |
| 6,174,329 B1 | 1/2001 | Callol et al. |
| 6,180,162 B1 | 1/2001 | Shigeru et al. |
| 6,240,616 B1 | 6/2001 | Yan |
| 6,253,443 B1 | 7/2001 | Johnson |
| 6,273,913 B1 | 8/2001 | Wright et al. |
| 6,287,249 B1 | 9/2001 | Tam et al. |
| 6,287,285 B1 | 9/2001 | Michal et al. |
| 6,287,331 B1 | 9/2001 | Heath |
| 6,290,721 B1 | 9/2001 | Heath |
| 6,299,604 B1 | 10/2001 | Ragheb et al. |
| 6,315,794 B1 | 11/2001 | Richter |
| 6,355,058 B1 | 3/2002 | Pacetti et al. |
| 6,395,230 B1 * | 5/2002 | Guerin et al. ............... 422/88 |
| 6,447,664 B1 | 9/2002 | Taskovics et al. |
| 6,475,644 B1 * | 11/2002 | Hampikian et al. ......... 428/655 |
| 6,592,764 B1 | 7/2003 | Stuky et al. |

(Continued)

FOREIGN PATENT DOCUMENTS

EP    0470 246 B1    6/1995

(Continued)

OTHER PUBLICATIONS

Kaisheva, et al., "Influence of the Surface Properties of SIC Particles on Their Codeposition with Nickel", Journal of the Electrochemical Society, vol. 151, No. 1, 2004, pp. C89-C96.

(Continued)

*Primary Examiner*—David Turocy
*Assistant Examiner*—Cachet I Sellman
(74) *Attorney, Agent, or Firm*—Richard Klein

(57) ABSTRACT

Disclosed herein are methods to create medical devices and medical devices including bioactive composite structures. The methods include using template-assisted electro- or electroless deposition or codeposition methods for providing implantable medical devices coated with bioactive composite structures and also include layering deposited or codeposited metal layers with layers of bioactive materials. In one use, the implantable medical devices of the present invention include stents with bioactive composite structure coatings.

8 Claims, No Drawings

U.S. PATENT DOCUMENTS

| | | | |
|---|---|---|---|
| 6,599,928 | B2 | 7/2003 | Kunz et al. |
| 6,716,444 | B1 | 4/2004 | Castro et al. |
| 6,730,064 | B2 | 5/2004 | Ragheb et al. |
| 2003/0060873 | A1 | 3/2003 | Gertner et al. |
| 2003/0096064 | A1 | 5/2003 | Suda et al. |
| 2004/0039438 | A1* | 2/2004 | Alt .............................. 623/1.15 |
| 2005/0119723 | A1* | 6/2005 | Peacock, III ............... 623/1.15 |

FOREIGN PATENT DOCUMENTS

| | | |
|---|---|---|
| EP | 0850 604 B1 | 7/1998 |
| EP | 0916 317 A1 | 5/1999 |
| EP | 0633 798 B1 | 5/2003 |
| WO | 91 12779 | 2/1991 |
| WO | 93 19803 | 10/1993 |
| WO | 99 25272 | 5/1999 |
| WO | 00 29501 | 5/2000 |
| WO | 01 14617 A1 | 3/2001 |
| WO | 01 15751 A1 | 3/2001 |
| WO | 01 70294 A2 | 9/2001 |
| WO | 02 058775 A2 | 8/2002 |
| WO | 02 078785 A2 | 10/2002 |
| WO | 03 045582 A1 | 6/2003 |
| WO | 2004 043292 A2 | 5/2004 |

OTHER PUBLICATIONS

Jeanmenne, Robert A., Jr., et al., "Electroless Plating on Medical Catheters," PF Online Feature Article, pp. 1-4.

Gertner, M.E., et al., "Electrochemistry and Medical Devices Friend or Foe?", The Electrochemical Society Interface, Fall 2003, pp. 20-24.

Schlesinger, Mordechay, et al., "Electroless Deposition of Nickel", Modern Electroplating, 2000, 4th Edition, pp. 667-737.

Gertner, Michae,l et al., "Drug Delivery From Electrochemically Deposited Thin Metal Films", Electrochemical and Solid-State Leters, Feb. 7, 2003, vol. 4, No. 4, pp. J4-J6.

Fields, William D., et al., "Electroless Nickel Plating", New Market Development, Allied-Kelite, Division of the Richardson Co., pp. 219-242.

Hajdu, Juan, "Chapter 7—Surface Preparation for Electroless Nickel Plating", pp. 193-206.

Geuze, Hans, et al., "Use of Colloidal Gold Particles in Double-Labeling Imunoelectron Microscopy of Ultrathin Frozen Tissue Section", The Journal of Cell Biology, vol. 89, Jun. 1981, pp. 653-665.

Mitchell, John, et al., "Phase Behaviour of Polyoxyethylene Surfactants with Water", J. Chem. Soc., Faraday Trans. 1, 1983, vol. 79, pp. 975-1000.

Attard, George S., et al., "Mesoporous Platinum Films from Lyotropic Liquid Crystalline Phases", Science, vol. 278, Oct. 31, 1997, pp. 838-840.

Lin, Victor S.-Y, et al., "A Porous Silicon-Based Optical Interferometric Biosensor", Science, vol. 278, Oct. 31, 1997, pp. 840-843.

Bartlett, P.N., et al., "Highly Ordered Macroporous Gold and Platinum Films Formed by Electrochemical Deposition Through Templates Assembled from Submicron Diameter Monodisperse Polystyrene Spheres", Chem. Matter, 2002, vol. 14, pp. 2199-2208.

Van Blaaderen, Alfons, et al., "Template-Directed Colloidal Crystallization", Nature, vol. 385, Jan. 23, 1997, pp. 321-324.

Jiang, P., et al., "Single-Crystal Colloidal Multilayers of Controlled Thickness", Chem. Mater, 1999, vol. 11, pp. 2132-2140.

Bartlett, Philip N., et al., "Electrochemical Deposition of Macroporous Platinum, Palladium and Cobalt Films Using Polystyrene Latex Sphere Templates", Chem. Commun., 2000, pp. 1671-1672.

Xu, Lianbin, et al., "Electrodeposited Nickel and Gold Nanoscale Metal Meshes with Potentially Interesting Photonic Properties", Chem. Commun. 2000, pp. 997-998.

Braun, Paul, et al., "Electrochemical Grown Photonic Crystals", Nature, vol. 409, Dec. 9, 1999, pp. 603-604.

Braun, Paul et al., "Electrochemically Fabrication of 3D Microperiodic Porous Materials", Adv. Mater, Apr. 4, 2001, vol. 13, No. 7, pp. 482-485.

Bartlett, P. N., et al., "Electrochemical Deposition of Macroporous Magnetic Networks Using Colloidal Templates", J. Mater. Chem., 2003, vol. 13, pp. 2596-2602.

Battlett, Philip N., "Electrodeposition of Nanostructured Films Using Self-Organizing Templates", The Electrochemical Society Interface, Winter 2004, pp. 28-33I.

Velev, O.D., et al., "A Class of Porous Metallic Nanostructure", Nature, vol. 401, Oct. 7, 1999, pp. 548.

* cited by examiner

METALLIC STRUCTURES INCORPORATING BIOACTIVE MATERIALS AND METHODS FOR CREATING THE SAME

CROSS-REFERENCES TO RELATED APPLICATIONS

This application is a continuation-in-part of U.S. patent application Ser. No. 10/497,198, filed on Dec. 13, 2004, now Abandoned, which is a continuation-in-part of U.S. patent application Ser. No. 10/196,296, filed on Jul. 15, 2002 and claims the benefit of PCT Application No. PCT/US02/38275 filed Nov. 27, 2002. It also claims the benefit of the filing dates of the following U.S. Provisional Patent Applications: 60/323,071, filed Sep. 19, 2001, 60/333,523, filed Nov. 28, 2001, and 60/364,083 filed Mar. 15, 2002. All of these patent applications are herein incorporated by reference in their entirety for all purposes.

FIELD OF THE INVENTION

The present invention relates to template-assisted electro- or electroless deposition or codeposition methods for providing implantable medical devices coated with bioactive composite structures. The present invention also provides methods for creating one or more layers of bioactive materials within a bioactive composite structure.

BACKGROUND OF THE INVENTION

In many circumstances, it is beneficial for an implanted medical device to release a bioactive material into the body once the device has been implanted. Such released bioactive materials can enhance the treatment offered by the implantable medical device, facilitate recovery in the implanted area and lessen the local physiological trauma associated with the implant. One type of device that has benefited from the inclusion of bioactive materials is stents. Stents are ridged, or semi-ridged, tubular scaffoldings that are deployed within the lumen (inner tubular space) of a vessel or duct during angioplasty or related procedures intended to restore patency (openness) to vessel or duct lumens. Stents generally are left within the lumen of a vessel or duct after angioplasty or a related procedure to reduce the risks of reclosure and restenosis, or re-occlusion. Including bioactive materials such as, for example and without limitation, rapamycin or paclitaxel on the surface of the implanted stent further helps to prevent restenosis.

One challenge in the field of implantable medical devices has been adhering bioactive materials to the surfaces of implantable devices so that the bioactive materials will be released once the device is implanted. One approach has been to include the bioactive materials in polymeric coatings. Polymeric coatings can hold bioactive materials onto the surface of implantable medical devices and release the bioactive materials via degradation of the polymer or diffusion into liquid or tissue (in this case the polymer is non-degradable). Degradable and non-degradable polymers such as polylactic acid, polyglycolic acid, and polymethylmethacrylate have been used in drug-eluting stents.

While polymeric coatings can be used to adhere bioactive materials to implanted medical devices, there are a number of problems associated with their use. First, it is difficult to predict the degradation kinetics of polymers. Consequently, it is difficult to predict how quickly a bioactive material in a polymeric coating will be released. If a drug releases from the polymeric coating too quickly or too slowly, the intended therapeutic effect may not be achieved. Second, in some cases, polymeric coatings produce pro-thrombotic and pro-inflammatory responses. These pro-thrombotic and pro-inflammatory effects lead to the necessity of prolonged anti-platelet therapies. Further, in the case of stents, these effects can exacerbate restenosis, a negative effect stents are designed to prevent. Third, adherence of a polymeric coating to a substantially different substrate, such as a stent's metallic substrate, is difficult due to differing characteristics of the materials (such as differing thermal expansion properties). The difficulty in adhering the two different material types often leads to inadequate bonding between the medical device and the overlying polymeric coating which can result in the separation of the materials over time. Such separation is an exceptionally undesirable property in an implanted medical device. Fourth, it is difficult to evenly coat a medical device with a polymeric coating. The uneven coating of a medical device can lead to unequal drug delivery across different portions of the device. This drawback is especially apparent in relation to small implantable medical devices, such as stents. Due to the viscosity of polymers during coating, it is difficult to evenly coat a medical device to faithfully replicate its form. Fifth, polymeric coatings are large and bulky relative to their bioactive material storage capacity. Sixth, when delivering a bioactive material to a patient over a longer time period, the bioactive material needs to be stabilized. Some polymeric coatings can not provide a stable storage environment for the bioactive material, in particular when liquid, such as blood, is able to seep into the polymeric coating. Seventh, polymeric coatings, which by their nature have large pores, can protect microorganisms in the interstices of the polymeric coating, thus increasing the risk of infection. Finally, polymeric coatings remain on the medical device once the bioactive materials they contained have fully-eluted. Thus, the negative effects of the polymeric coating remain even after the bioactive materials are no longer providing continued treatment.

Sintered metallic structures can be used as an alternative to polymeric coatings. In a typical sintering process, small particles of metal are joined by an epoxy and then treated with heat and/or pressure to weld them together and to the substrate. A porous metallic structure has then been created. While effective in some instances, sintered metallic structures have relatively large pores. When a bioactive material is loaded into the pores of a sintered metallic structure, the larger pore size can cause the biologically active material to be released too quickly. As noted above, it would be desirable to have the ability to increase the bioactive material storage capacity in a bioactive composite material so that, for example, the bioactive material can be released to a patient over a long period of time.

While several alternative methods for coating stents and other implantable medical devices with bioactive materials have also been proposed, these methods also suffer from drawbacks including those resulting from processing limitations in relation to the underlying substrate or bioactive agent to be coated; inability to obtain even distribution of coatings or bioactive materials; problems with adhesion; biocompatibility issues (e.g. toxicity, or other adverse biological response); complexity of processing; size; density (and thus volume of drug that can be held and released); timing of drug release; high electrical impedance; low radiopacity; or an impact of the coating on the underlying substrate's intended function (e.g. mechanical properties, expansion characteristics, electrical surface conduction, radiopacity, etc.). Thus, notwithstanding certain benefits that may be provided by polymeric coatings, sintering or other alternative methods for coating implantable medical devices with bioactive materials, there is still room for improvement. Specifically, it would be beneficial if a coating process and matrix could be provided that overcomes one or more of the above-mentioned limitations.

SUMMARY OF THE INVENTION

The present invention addresses many of the drawbacks associated with previously-available methods of loading bioactive materials onto implantable medical devices, by providing methods and materials for loading bioactive materials directly into a metal layer formed on the surface of the implantable medical device. Alternatively, the present invention also provides creating approximately alternating layers of bioactive material layers and metal layers on the surface of an implantable medical device. Loading bioactive materials directly into a metal layer or in approximately alternating layers within a metal layer is advantageous for many reasons. First, the deposited metals, unlike polymers, are not prothrombotic or pro-inflammatory. Because polymers are not used to carry the bioactive materials, once the bioactive materials have eluted from the implantable medical device, only bare metal, which is not pro-thrombotic or pro-inflammatory, is left behind. Thus, no negative effects of including the bioactive materials remain once the bioactive materials have fully eluted. Second, when a metal layer is deposited onto an implantable medical device that is also made from a metal, the metal layer and underlying device do not have substantially different characteristics, so the risk of separation is diminished significantly. Third, deposition of a metal layer in accordance with the methods of the present invention allows for an even coating of implantable medical devices regardless of their size or geometry. Fourth, harsh processing conditions that may damage bioactive materials during the coating or loading process, are not required and the ability to control the percentage of bioactive materials present within or around the metal layer can be easily controlled. Finally, the methods according to embodiments of the present invention are economical and scaleable, and are more cost-effective than other methods of forming bioactive composite structures.

Specifically, the methods of the present invention provide methods to create pores within metal layers deposited onto the surface of implantable medical devices that can be loaded with bioactive materials. In one embodiment of the methods of the present invention, pores are created by forming a template on the surface of the implantable medical device before the metal layer is created. Once the metal layer has been created on the surface of the implantable medical device around the template, the template can be removed, leaving small pores within the metal layer that can then be post-loaded with bioactive materials. In another embodiment of the methods of the present invention, bioactive materials are "codeposited" concurrently with metal ions forming the metal layer around the template. In this embodiment, after template removal and post-loading, bioactive materials are found both within the pores created by the removed template and within the metal layer itself. In another embodiment of the present invention, layers of bioactive materials alone are created between and among layers of deposited metal alone or layers of codeposited metal and bioactive materials.

In one embodiment, the methods of the present invention include creating a template on the surface of a substrate; providing a solution comprising metal ions; contacting the substrate with the solution; forming a composite structure (such as a metal layer) on portions of the substrate not covered by the template using an electrochemical process; removing the template from the substrate after the formation of the composite structure thus leaving pores in the structure; and loading bioactive material(s) into the pores thus forming a bioactive composite structure over the substrate.

In another embodiment of the methods of the present invention, the electrochemical process is an electrodeposition process. In another embodiment of the methods of the present invention, the electrochemical process is an electroless deposition process.

In another embodiment of the methods of the present invention, the provided solution also includes bioactive materials, the electrodeposition process is an electrocodeposition process and the composite structure formed after the contacting is a bioactive composite structure. In another embodiment of the methods of the present invention, the provided solution also includes bioactive materials, the electroless deposition process is an electroless codeposition process, and the composite structure formed after the contacting is a bioactive composite structure.

In another embodiment of the methods of the present invention, the substrate is a stent.

In another embodiment of the methods of the present invention, a topcoat is formed over the bioactive composite structures.

In another embodiment of the methods of the present invention, the bioactive materials are selected from the group consisting of rapamycin, paclitaxel and 3-hydroxy-3-methylglutaryl coenzyme A (HMG-CoA) reductase inhibitors.

The embodiments of the present invention also include medical devices. In one embodiment, the medical device comprises a bioactive composite structure that is formed by creating a template on the surface of a substrate; providing a solution comprising metal ions; contacting the substrate and the solution; forming a composite structure on portions of the substrate not covered by the template using an electrochemical process; removing the template from the substrate after the formation of the composite structure thus leaving pores in the structure; and loading bioactive material(s) into the pores thus forming a bioactive composite structure over the substrate.

In another embodiment of the medical devices of the present invention, the electrochemical process is a electrodeposition process. In another embodiment of the medical devices of the present invention, the electrochemical process is a electroless deposition process.

In another embodiment of the medical devices of the present invention, the provided solution also includes bioactive materials, the electrodeposition process is an electrocodeposition process, and the composite structure formed after the contacting is a bioactive composite structure. In another embodiment of the medical devices of the present invention, the provided solution also includes bioactive materials, the electroless deposition process is an electroless codeposition process and the composite structure formed after the contacting is a bioactive composite structure.

In another embodiment of the medical devices of the present invention, the substrate is a stent.

In another embodiment of the medical devices of the present invention, the medical device includes a topcoat over the bioactive composite structures.

In another embodiment of the medical devices of the present invention, the bioactive materials are selected from the group consisting of rapamycin, paclitaxel and HMG-CoA reductase inhibitors.

The embodiments of the present invention also include a stent wherein the stent comprises a bioactive composite structure and the bioactive composite structure comprises, pores, metal material around the pores and bioactive material(s) within the pores and the metal material.

In another embodiment of the stents of the present invention, the bioactive material is selected from the group consisting of rapamycin, paclitaxel and HMG-CoA reductase inhibitors.

In another embodiment of the stents of the present invention, the stent further comprises a topcoat formed over the bioactive composite structure.

The present invention also includes methods to create implantable medical devices with approximately alternating layers of metals and bioactive materials. In one embodiment, the methods of the present invention comprise providing a first solution comprising metal ions; contacting a substrate with the first solution; forming a first metal layer on the substrate using an electrochemical process; applying a bioactive material(s) to said first metal layer; contacting said substrate with the first solution or a second solution; forming a second layer metal layer on said substrate using an electrochemical process.

In another embodiment of the methods of the present invention, the electrochemical process is an electrodeposition process. In another embodiment of the methods of the present invention, the electrochemical process is an electroless deposition process.

In another embodiment of the methods of the present invention, the first solution, the second solution or the first and the second solution further comprise bioactive materials and the first metal layer, the second metal layer or the first and second metal layer further comprise codeposited bioactive materials.

In another embodiment of the methods of the present invention, the substrate is a stent.

In another embodiment of the methods of the present invention, the bioactive material(s) are selected from the group consisting of rapamycin, paclitaxel and HMG-CoA reductase inhibitors.

The present invention also includes medical devices with approximately alternating metal and bioactive material(s) layers. In one embodiment of the present invention the medical device comprises a bioactive composite structure wherein said bioactive composite structure is formed by: providing a first solution comprising metal ions; contacting a substrate with the first solution; forming a first metal layer on the substrate using an electrochemical process; applying a bioactive material(s) to the first metal layer; contacting the substrate with the first solution or a second solution; forming a second layer metal layer on the substrate using an electrochemical process.

In another embodiment of the medical device of the present invention, the electrochemical process is an electrodeposition process. In another embodiment of the medical device of the present invention, the electrochemical process is an electroless deposition process.

In another embodiment of the medical device of the present invention, the first solution, the second solution or the first and the second solution further comprise bioactive materials and the first metal layer, the second metal layer or the first and second metal layer further comprise codeposited bioactive materials.

In another embodiment of the medical device of the present invention, the substrate is a stent.

In another embodiment of the medical device of the present invention, the bioactive material(s) are selected from the group consisting of rapamycin, paclitaxel and HMG-CoA reductase inhibitors.

The present invention also includes stents with approximately alternating layers of metal and bioactive materials. In one embodiment of the stents of the present invention, the stent comprises a bioactive composite structure wherein the bioactive composite structure comprises alternating layers of metal and bioactive materials and wherein the alternating layers are formed by: providing a first solution comprising metal ions; contacting a substrate with the first solution; forming a first metal layer on the substrate using an electrochemical process; drying the substrate after the contacting with the solution; applying a bioactive material(s) to the first metal layer;

drying the substrate after the applying of the bioactive material(s); contacting the substrate with a second solution; and forming a second layer metal layer on the substrate using an electrochemical process.

DETAILED DESCRIPTION

I. Definitions

Some terms that are used herein are described as follows.

The term "bioactive material(s)" refers to any organic, inorganic, or living agent that is biologically active or relevant. For example, a bioactive material can be a protein, a polypeptide, a polysaccharide (e.g. heparin), an oligosaccharide, a mono- or disaccharide, an organic compound, an organometallic compound, or an inorganic compound. It can include a living or senescent cell, bacterium, virus, or part thereof. It can include a biologically active molecule such as a hormone, a growth factor, a growth factor-producing virus, a growth factor inhibitor, a growth factor receptor, an anti-inflammatory agent, an antimetabolite, an integrin blocker, or a complete or partial functional insense or antisense gene. It can also include a man-made particle or material, which carries a biologically relevant or active material. An example is a nanoparticle comprising a core with a drug and a coating on the core. Such nanoparticles can be post-loaded into pores or co-deposited with metal ions.

Bioactive materials also can include drugs such as chemical or biological compounds that can have a therapeutic effect on a biological organism. Bioactive materials include those that are especially useful for long-term therapy such as hormonal treatment. Examples include drugs for contraception and hormone replacement therapy, and for the treatment of diseases such as osteoporosis, cancer, epilepsy, Parkinson's disease and pain. Suitable biological materials can include, e.g., anti-inflammatory agents, anti-infective agents (e.g., antibiotics and antiviral agents), analgesics and analgesic combinations, antiasthmatic agents, anticonvulsants, antidepressants, antidiabetic agents, antineoplastics, anticancer agents, antipsychotics, and agents used for cardiovascular diseases such as anti-restenosis and anti-coagulant compounds.

Bioactive materials also can include precursor materials that exhibit the relevant biological activity after being metabolized, broken-down (e.g. cleaving molecular components), or otherwise processed and modified within the body. These can include such precursor materials that might otherwise be considered relatively biologically inert or otherwise not effective for a particular result related to the medical condition to be treated prior to such modification.

Combinations, blends, or other preparations of any of the foregoing examples can be made and still be considered bioactive materials within the intended meaning herein. Aspects of the present invention directed toward bioactive materials can include any or all of the foregoing examples.

The term "medical device" refers to an entity not produced in nature, which performs a function inside or on the surface of the human body. Medical devices include, but are not limited to, biomaterials, drug delivery apparatuses, vascular conduits, stents, catheters, plates, screws, spinal cages, dental implants, dental fillings, braces, artificial joints, embolic devices, ventricular assist devices, artificial hearts, heart valves, venous filters, staples, clips, sutures, prosthetic meshes, pacemakers, pacemaker leads, defibrillators, neurostimulators, neurostimulator leads, and implantable or external sensors. Medical devices are not limited by size and include micromechanical systems and nanomechanical systems which perform a function in or on the surface of the human body. Embodiments of the invention include such medical devices.

The term "substrate" refers to any physical object that can be submerged in a bath and subjected to electro- or electroless deposition with metal ions or electro- or electroless codeposition with metal ions and bioactive materials.

The terms "implants" or "implantable" refers to a category of medical devices, which are implanted in a patient for some period of time. They can be diagnostic or therapeutic in nature, and long- or short-term.

The term "self-assembly" refers to a nanofabrication process of forming a material or coating, which proceeds spontaneously from a set of ingredients. A common self-assembly process includes the self-assembly of an organic monolayer on a substrate. One example of this process is the binding of linear organic molecules to a substrate. In this example, each molecule contains a thiol group (S—H moiety) and the thiol group of each molecule couples to the substrate while the other end of the molecule extends away from the substrate. The process of electroless deposition or codeposition, which continues spontaneously and auto-catalytically from a set of ingredients, can also be considered a self-assembly process.

The term "stents" refers to devices that are used to maintain patency of a body lumen or interstitial tract. There are two categories of stents; those which are balloon expandable (e.g., stainless steel) and those which are self-expanding (e.g., nitinol). Stents are currently used in peripheral, coronary, and cerebrovascular vessels, the alimentary, hepatobiliary, and urologic systems, the liver parenchyma (e.g., porto-systemic shunts), and the spine (e.g., fusion cages). In the future, stents will be used in smaller vessels (currently minimum stent diameters are limited to about 2 millimeters). For example, they will be used in the interstitium to create conduits between the ventricles of the heart and coronary arteries, or between coronary arteries and coronary veins. In the eye, stents are being developed for the Canal of Schlem to treat glaucoma.

The phrase "electrochemical process" as used herein means an electrodeposition (also known as electroplating) or electroless deposition process or an electrocodeposition or electroless codeposition process as described herein. A deposition process refers to deposition of metal alone through an electro- or electroless process (although, as will be understood by one of skill in the art, an electroless process also involves ions of a reducing agent). A codeposition process refers to approximately concurrent deposition of metal and bioactive materials through an electro- or electroless process.

The term "solution" as used herein means any liquid in which an electrochemical process takes place and can be, without limitation, an electrolyte solution, an electrochemical solution and an electroless bath.

The phrase "composite structure" as used herein refers to the material overlying a substrate that results from an electrochemical deposition process that does not include any bioactive materials.

The phrase "bioactive composite structure" as used herein refers to the material overlying a substrate that results from an electrochemical deposition or codeposition process that includes bioactive materials. As a non-limiting example, a substrate can undergo template formation and an electrochemical deposition process. After the electrochemical deposition process, the material overlying the substrate would be a composite structure. Once the template is removed and bioactive materials post-loaded into the created pores, the material becomes a bioactive composite structure. Alternatively, a substrate can undergo template formation and an electrochemical codeposition process. After the electrochemical codeposition process, the material overlying the substrate would be a bioactive composite structure even before template removal and post loading of bioactive materials into the pores because bioactive materials were included in the metal layer during codeposition. As a final non-limiting example, substrates coated with approximately alternating metal and bioactive material layers are biocomposite structures.

The phrase "approximately alternating" as used herein means that generally, when layered, metal layers and bioactive material layers will be placed in a conventionally alternating arrangement (i.e., metal layer; bioactive material layer; metal layer; bioactive material layer; etc.). In some circumstances, however, due to differing thicknesses in portions of a layer, one metal layer may actually come into contact with a different metal layer (and likewise, one bioactive material layer could come into contact with another bioactive material layer). This contact is within the scope of "approximately alternating." Further, the layers of metal and bioactive materials need not be the same width, and the layers are not required to be in a one-to-one conventionally alternating pattern. For instance, in one embodiment it may be desirable to coat two layers of metal between layers of bioactive materials (which would create one thicker metal layer).

II. Methods of Manufacture

Embodiments of the invention include methods of coating substrates including implantable medical devices with bioactive materials to form bioactive composite structures. In one embodiment of the methods of the present invention, a template is formed on the substrate prior to forming a metal layer or metal layer with bioactive materials on the surface of the implantable medical device. Once the template is formed, metal ions or metal ions and bioactive materials are deposited onto the surface of the implantable medical device not covered by the template to form a composite structure. After this layer is created, the template is removed, leaving pores which can then be loaded with bioactive materials. In another embodiment, regardless of whether a template is formed, approximately alternating layers of metal and bioactive materials can be placed on the surface of an implantable medical device.

A. Substrate and Substrate Preparation

The substrates of the present invention can be prepared in any suitable manner prior to forming a template or bioactive composite structure on its surface. For example, the substrate surface can be sensitized and/or catalyzed prior to performing electroless deposition or codeposition processes (if the surface of the substrate is not itself autocatalytic). Metals such as tin (Sn) can be used as sensitizing agents. Many metals (e.g., nickel (Ni), cobalt (Co), copper (Cu), silver (Ag), gold (Au), palladium (Pd), platinum (Pt)) are good auto catalysts. Palladium, Pt, and Cu are examples of "universal" nucleation center-forming catalysts. In addition, many non-metals are good catalysts as well.

Before template formation or creation of a metal layer, metal layer with bioactive materials or approximately alternating layers of metals and bioactive materials, the substrate also can be rinsed and/or precleaned if desired. Any suitable rinsing or pre-cleaning liquid or gas could be used to remove impurities from the surface of the substrate before creating a template, metal layer, metal layer with bioactive materials or approximately alternating layers of metals and bioactive materials. Also, in some embodiments involving electroless deposition or codeposition, distilled water can be used to rinse the substrate after sensitizing and/or catalyzing, but before performing the electroless process in order to remove loosely attached molecules of the sensitizer and/or catalyst.

Prior to creating a template, metal layer, metal layer with bioactive materials or approximately alternating layers of metals and bioactive materials, the substrates of the present invention also can undergo an anodic process. In this process, the substrate is submerged in a hydrochloric acid bath. Current is passed through the hydrochloric acid bath, creating small pits in the substrate. Such pits promote adhesion. Also, a sensitizing agent and/or catalyst can be deposited on the substrate to assist in the creation of nucleation centers leading to the formation of the bioactive composite structure. Loosely adhered nucleation centers can also be removed from the surface of the substrate using, for example, a rinsing process.

The templates that can be used in accordance with the present invention include the use of nano- or microscale template material and/or processes. For instance, an example of nanoscale material suitable for template formation in accordance with the present invention is an organic material such as oactaethyl monohexadecyl or an inorganic colloid, such as, for example, colloidal gold. These colloids self-assemble into random close-packed or face-centered cubic (fcc) arrays that can be utilized as templates for the creation of inverse structures with periodicities ranging from less than 100 nm to greater than 10 μm.

In one embodiment of the methods of the present invention, a colloidal crystal template can be assembled from monodisperse, negatively charged polysterene latex microspheres ranging in diameter from approximately 300 nm to approximately 1000 nm. The latex particles used are diluted into approximately 10 mL of deionized water and then deposited into packed layers. To improve the quality of the arrays, approximately 0.15 wt % of a nonionic surfactant, such as, for example and without limitation, Polysorbate 20 can be added to the latex suspension. The dilute microspheres accumulate on the substrate surface into packed 3D ordered layers with a thickness of about 35 microns.

In another embodiment of the methods of the present invention, a colloidal template can be formed by slow sedimentation of approximately 1 μm silica spheres (Duke Scientific, Inc.) from water onto the substrate followed by careful drying in approximately 90% relative humidity. In another embodiment, a template can be formed by the slow drying of an aqueous suspension of approximately 0.466 μm polysterene colloidal particles (carboxyl/suflonate surface termination, Interfacial Dynamics, Inc.) onto a substrate. Monodisperse polysterene latex spheres (diameters 200, 500, 750, 1000 (±20) nm) also can be obtained from Alfa Aesar as 2.5 wt % solutions in water.

A substrate also can be immersed in a "striking" bath as described in U.S. patent application Ser. No. 10/701,262 filed on Nov. 2, 2004. Specifically, in a striking bath, a current is applied across the substrate causing metal ions to move to the device and plate the surface. This step causes an intermediate or "strike" layer to be formed on the surface of the substrate. Metal ions for this first striking bath are chosen to be compatible with the material making up the substrate itself. For example, if the underlying substrate is made of cobalt chrome, cobalt ions are used. It has been found that this strike layer improves overall adherence of the coating to the substrate as well as increasing the rate of deposition during subsequent electrochemical processing. In one embodiment, when striking is performed, the substrate is rinsed with water prior to subsequent electrochemical processing.

B. Electrochemical Processes

After a substrate has been prepared according to any of the treatments described above, the substrate undergoes an electro- or electroless deposition or codeposition process to create a metal layer, metal layer with bioactive materials or approximately alternating layers of metals and bioactive materials on the exposed surface of the substrate not covered by the template. For purposes of the following discussion, deposition refers to deposition of metal alone through an electro- or electroless process (although, as will be understood by one of skill in the art, an electroless process also involves ions of a reducing agent). Codeposition refers to deposition of metal and bioactive materials through an electro- or electroless process.

In electrodeposition, an anode and cathode are electrically coupled through an electrolyte. As current passes between the electrodes, metal is deposited on the cathode while it is either dissolved from the anode or originates from the electrolyte solution. Electrodeposition processes are well known in, for example, the metal plating industry and in the electronics industry.

An exemplary reaction sequence for the reduction of metal in an electrodeposition process is as follows:

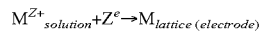

$$M^{Z+}_{solution} + Z^{e-} \rightarrow M_{lattice\ (electrode)}$$

In this equation, M is a metal atom, $M^{Z+}$ is a metal ion with z charge units and e is an electron (carrying a unit charge). The reaction at the cathode is a reduction reaction and is the location where electrodeposition occurs. There is also an anode where oxidation takes place. To complete the circuit, an electrolyte solution is provided. The oxidation and reduction reactions occur in separate locations in the solution. In an electrodeposition process, the substrate is a conductor as it serves as the cathode in the process. Specific electrodeposition conditions such as the current density and metal ion concentration can be determined by those of ordinary skill in the art.

When electrodeposition is used to form a metal layer around a template, it can be beneficial to lightly sinter the template before the electrodeposition to prevent cracking and breakage of the template during electrodeposition. A silica colloid can be sintered at approximately 300° C. for approximately 30 minutes. A polysterene colloid can be sintered at approximately 105° C. for approximately 60 minutes.

Electroless deposition processes can also be used in accordance with the methods of the present invention. In an electroless deposition process, current does not pass through a solution. Rather, the oxidation and reduction processes both occur at the same "electrode" (i.e., on the substrate). It is for this reason that electroless deposition results in the deposition of a metal and an anodic product (e.g., nickel and nickel-phosphorus).

In an electroless deposition process, the fundamental reaction is:

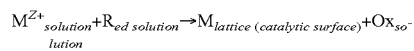

$$M^{Z+}_{solution} + R_{ed\ solution} \rightarrow M_{lattice\ (catalytic\ surface)} + Ox_{solution}$$

In this equation, R is a reducing agent, which passes electrons to the substrate and the metal ions. Ox is the oxidized byproduct of the reaction. In an electroless process, electron transfer occurs at substrate reaction sites (initially the nucleation sites on the substrate; these then form into sites that are tens of nanometers in size). The reaction is first catalyzed by the substrate and is subsequently auto-catalyzed by the reduced metal as a metal matrix forms.

The electroless deposition bath comprises at least a reducing agent and metal ions alone or a reducing agent, metal ions and a bioactive material. The solvent that is used in the electroless deposition bath can include water so that the deposition bath is aqueous. Deposition conditions such as the pH, deposition time, bath constituents, and deposition temperature can be chosen by those of ordinary skill in the art.

During the electro- or electroless deposition processes of the present invention, metal ions deposit over the surface of the substrate. When bioactive materials are included in the solution or bath during the electro- or electroless codeposition processes, without being bound by theory, it is believed that tens of nanometers of metal first deposit onto the surface of the stent. Following this deposition of tens of nanometers of metal, metal ions and bioactive materials codeposit onto the already deposited metal. Thus, the bioactive material and the metal atoms can deposit substantially simultaneously. When codepositing metal atoms and bioactive materials, the bioactive material is incorporated into the metal matrix. These crystallites confine the bioactive material in the formed bioactive composite structure.

By codepositing the bioactive material along with the metal, the concentration of the bioactive material in the bioactive composite structure can be high. Moreover, the problems associated with impregnating porous structures with bioactive materials are not present in the electro- or electroless codeposition methods of the present invention.

As an example of the codeposition methods of the present invention, in one embodiment after template formation on the surface of the substrate as described above, a nickel-phosphorous alloy matrix can be electrolessly codeposited on a substrate along with a bioactive material such as a drug. In one embodiment, the substrate can be activated and/or catalyzed (using, e.g., Sn and/or Pd) prior to metallizing. To produce the alloy matrix, the electroless deposition bath can contain $NiSO_4$ (26 g/L), $NaH_2PO_2$ (26 g/L), Na-acetate (34 g/L) and malic acid (21 g/L). The bath can contain ions derived from the previously mentioned salts. A bioactive material is also in the bath. Non-limiting examples of bioactive materials that can be included in the presently-described bath include 1 mg paclitaxel, 1 mg rapamycin, and/or 1 mg of a 3-hydroxy-3methylglutaryl coenzyme A (HMG-CoA) reductase inhibitor, such as, but not limited to, cervistatin. In this embodiment, sodium hypophosphite is the reducing agent and nickel ions are reduced by the sodium hypophosphite. The temperature of the bath is from about room temperature to about 95° C. depending on desired deposition time. The pH is generally from about 5 to about 7 (these processing conditions could be used in other embodiments). The substrate to be coated is then immersed in the bath and a bioactive composite structure is formed on the exposed surface of the substrate after a predetermined amount of time. The Ni ions in solution deposit onto the exposed surface of the substrate as pure nickel (reduction reaction) along with nickel-phosphorous alloy (oxidation reaction); the bioactive material codeposits along the crystallite and grain boundaries of the deposited metal matrix to form a bioactive composite structure. Typically, the amount of phosphorous ranges from <1% to >25% (mole %) and can be varied by techniques known to those skilled in the art. After the codeposition process, the template can be removed and the resulting pores can be post-loaded with additional bioactive materials (see infra for exemplary template removal and post-loading processes).

Any suitable source of metal ions can be used in embodiments of the invention. The metal ions in the bath can be derived from soluble metal salts before they are in the bath. In solution, the ions forming the metal salts can dissociate from each other. Non-limiting examples of suitable metal salts for nickel ions include nickel sulfate, nickel chloride, and nickel sulfamate. Non-limiting examples of suitable metal salts for copper ions include cupric and cuprous salts such as cuprous chloride or sulfate. Non-limiting examples of suitable metal salts for tin cations can include stannous chloride or stannous floroborate. Other suitable salts useful for depositing other metals are known in the electroless deposition art. Different types of salts can be used if a metal alloy matrix is to be formed.

The bath also can include a reducing agent, complexing agents, stabilizers, and buffers. The reducing agent reduces the oxidation state of the metal ions in solution so that the metal ions deposit on the surface of the substrate as metal. Non-limiting examples of reducing compounds include boron compounds such as amine borane and phosphites such as sodium hypophosphite. Complexing agents are used to hold the metal in solution. Buffers and stabilizers are used to increase bath life and improve the stability of the bath. Buffers are used to control the pH of the bath. Stabilizers can be used to keep the solution homogeneous. Non-limiting examples of stabilizers include lead, cadmium, copper ions, etc. Reducers, complexing agents, stabilizers and buffers are well known in the electroless deposition art and can be chosen by those of ordinary skill in the art.

The metallic matrix of the bioactive composite structure formed during the electro- or electroless deposition or codepostion methods of the present invention can include any suitable metal. The metal in the metallic matrix can be the same as or different from the substrate metal (if the substrate is metallic). The metallic matrix can include, for example, noble metals or transition metals. Suitable metals include, but are not limited to, nickel, copper, cobalt, palladium, platinum, chromium, iron, gold, and silver and alloys thereof. Examples of suitable nickel-based alloys include Ni—Cr, Ni—P, and Ni—B. Any of these or other metallic materials can be deposited using a suitable electro- or electroless deposition or codeposition process. Appropriate metal salts can be selected to provide appropriate metal ions in the bath for the metal matrix that is to be formed.

After contacting the substrate with the solution or bath, a composite structure or a bioactive composite structure is formed on the substrate using an electro- or electroless deposition or codeposition process. Whether the structure is a composite structure or a bioactive composite structure at this stage depends on whether a bioactive material is included in the solution or bath during the initial immersion. In this embodiment, after forming the composite or bioactive composite structure, the structure/substrate combination is removed from the solution or bath and subjected to subsequent processing (see Section C, infra).

In one embodiment of the present invention, instead of codepositing metal ions and bioactive materials, metal ions and bioactive materials are placed onto the surface of an implantable medical device in approximately alternating layers. The metal layers can be created according to the electro- or electroless deposition methods as previously described. In one non-limiting example, approximately alternating layers of metal and bioactive materials are created according to the following procedure: the substrate, an implantable medical device, is cleaned with an alkaline cleaner after sandblasting and then rinsed with deionized water. After rinsing with deionized water, the substrate is immersed in a $SnCl_2$ solution for three minutes at room temperature. Following this immersion, the substrate is again rinsed with deionized water and then immersed in a $PdCl_2$ solution for three minutes at room temperature. After another rinse in deionized water, the substrate is immersed in a low-phosphorous (P) content Ni—P bath that has been raised up to about 85-90° C. for about 90 seconds. After this immersion a metal layer has been created on the surface of the substrate. After forming this metal layer, the substrate is rinsed with deionized water and dried with $N_2$ gas. A first layer of bioactive materials is then created by micropipetting 50 mL of a highly concentrated bioactive material (such as, without limitation, paclitaxel) with 0.04 g hexadecyltrimethylammonium bromide (HTAB) onto the substrate. After micropipetting the bioactive material onto the substrate, the substrate is dried with low pressure $N_2$ gas. These steps of micropipetting the bioactive materials and drying with low pressure $N_2$ gas can be repeated until a layer of bioactive materials with a desired thickness has been created. Next, the substrate is immersed in a high-P content Ni—P bath that has been raised up to about 50° C. for approximately three minutes. Following this immersion, the substrate is rinsed with deionized water and dried with $N_2$ gas. At this stage, the substrate has a metal layer followed by a bioactive material layer followed by a metal layer. The steps may be repeated as desired to create a desired number of layers.

While the above-described layer creating method describes layers of metal alone approximately alternating with layers of bioactive materials, it should be understood that in yet another embodiment the metal layer could also include codeposited bioactive materials, as described supra. In this embodiment, the approximately alternating layers would be metal with codeposited bioactive materials and layers of bioactive materials alone. Further, these layering embodiments of the present invention can occur on bare implantable medical devices or implantable medical devices that have had templates previously created on their surface.

C. Subsequent Processing

After electro- or electroless deposition, codeposition or layering onto the surface of the substrate, the device can be processed further to alter its clinical features.

1. Template Removal

After the electro- or electroless deposition, codeposition process or layering, in embodiments containing a template, the template is removed to create pores that can be post-loaded with bioactive materials. In one embodiment, the template can be removed by calcinations in which the temperature is ramped at approximately 0.2° C./minute to approximately 300° C., where it is maintained for approximately 30 minutes before cooling. The templates of the present invention also can be removed by chemical oxidation or solvent dissolution at room temperature. In another embodiment, the template can be removed with ultraviolet light. In another embodiment, if the template material is metallic and the electrochemical potential of the template is lower than the material deposited around the template, an electrochemical process can be used to selectively remove the template material. When the template is removed, pores are left behind in the composite or biocomposite structure which can then be filled with another substance (e.g. a bioactive material).

Methods to load bioactive materials into composite or biocomposite structure pores are known in the art. One such method is described in detail. In this method, a bioactive material is added to a first fluid. The bioactive material is dispersed throughout the first fluid so that it is in a true solution, saturated or supersaturated with the first fluid or suspended in fine particles in the first fluid. If the bioactive material is suspended in particles in the first fluid, the pore size and the diameter of the opening of the composite or biocomposite structure pores are to be sufficiently large in comparison to the size of the particles to facilitate loading and unloading of the pores of the substrate.

The first fluid can be virtually any solvent that is compatible with the bioactive material. A suitable first fluid typically has a high capillary permeation. Capillary permeation or wetting is the movement of fluid on a solid substrate driven by interfacial energetics. Capillary permeation is quantitated by a contact angle, defined as the angle at the tangent of the first fluid droplet in fluid phase that has taken an equilibrium shape on a solid surface. A low contact angle means a higher wetting liquid. A suitably high capillary permeation corresponds to a contact angle less than about 90°.

A high capillary permeation and a viscosity not greater than about ten centipoise allows the first fluid to penetrate into the pores of the substrate more quickly, eliminating a requirement to apply the first fluid to the substrate for a prolonged period of time. The first fluid can be volatile, facilitating its evaporation. Useful examples of some first fluids include, but are not limited to, acetone, ethanol, methanol, isopropanol, tetrahydrofuran, and ethyl acetate. The first fluid is applied to a porous substrate, for example by immersing or spraying the solvent in procedures that are well-known to one having ordinary skill in the art.

The first fluid is applied for a predetermined period of time, the specific time depending on the capillary permeation and viscosity of the first fluid, the volume of the pores, and the amount of bioactive materials to be deposited. Therapeutic parameters such as the concentration of the bioactive material in the solvent and dosages depend on the duration of local release, the cumulative amount of release, and desired rate of release. Correlations and interrelations between the therapeutic parameters are well-known to one having ordinary skill in the art and are simply calculated.

After applying the first fluid for a selected duration, the first fluid is removed from the substrate. In one example, the first fluid is removed by evaporation in ambient pressure, room temperature, and anhydrous atmosphere and/or by exposure to mild heat (e.g., 60° C.) under a vacuum condition.

After removal from the first fluid, the substrate typically has a clustered or gross formation of bioactive material gathered on its surface. The cluster is generally removed by immersing the substrate in a second fluid and agitating the substrate via mechanical perturbation techniques, such as vortexing or vigorous shaking. The second fluid is a non-solvent so that the bioactive material does not significantly dissolve in the second fluid. The non-solvent second fluid can have a low capillary permeation or a contact angle greater than about 90° and a viscosity not less than about 0.5 centipoise so that the second fluid is not capable of significantly penetrating into the pores during the process of agitation. Examples of a second fluid include, but are not limited to, saturated hydrocarbons or alkanes, such as hexane, heptane, and octane.

After immersion in the second fluid, the substrate is rinsed in a third fluid. The third fluid is typically a solvent to facilitate dissolution of the bioactive material. The third fluid generally has a low capillary permeation, corresponding to a contact angle greater than about 90°. The third fluid has a viscosity of not less than about 1.0 centipoise and is therefore incapable of significantly penetrating into the pores during the rinsing stage. In one embodiment, the third fluid can be highly volatile, for example having a boiling point of not greater than about 60° C. at 1 atm. Accordingly, the third fluid is capable of rapidly evaporating. Rapid evaporation of the third fluid causes the third fluid to be removed from the substrate prior to any significant penetration of the third fluid in the pores. A useful example of a highly volatile third fluid includes, but is not limited to, Freon® (Freon® is a registered Trademark of E.I. du Pont de Nemours and Company Corporation, 1007 Market St., Wilmington, Del. 19898).

Rinsing with the third fluid is conducted rapidly for example in a range from 1 second to about 15 seconds, the exact duration depending on the solubility of the bioactive material in the solvent. Extended duration of exposure of the third fluid to the substrate may lead to the penetration of the third fluid into the pores.

The rinsing step is repeated, if desired, until all traces of bioactive material are removed from the surface of the substrate. Useful examples of third fluids include but are not limited to, dimethylsulfoxide (DMSO), water, DMSO in an aqueous solution, glyme, and glycerol. The third fluid is removed from the substrate body using a technique such as evaporation in ambient pressure, room temperature and anhydrous atmosphere and/or by exposure to mild heat (e.g., 60° C.) under vacuum condition. The first, second and third fluids are selected to not affect the characteristics and composition of the bioactive material adversely.

In some embodiments, a surface of the substrate is coated with a bioactive material in addition to having a bioactive material deposited in the pores. A coating of bioactive material on the surface of the substrate is formed by adding the bioactive material to the third fluid rinse. The bioactive material is dispersed through the third fluid to form a true solution with the third fluid, rather than a dispersion of fine particles.

Alternative methods that can be used to load bioactive materials into the composite structure pores of the present invention include high pressure loading. In this method, the substrate is placed in a bath of the desired drug or drugs and subjected to high pressure or, alternatively, subjected to a vacuum. In the case of the vacuum, the air in the pores of the metal stent is evacuated and replaced by the drug-containing solution. Additional methods of loading bioactive materials into pores are disclosed in U.S. Pat. No. 6,379,381 issued to Hossainy et al., which is hereby incorporated by reference for all it contains regarding bioactive material loading.

2. Optional Top Coat Formation

If desired, a topcoat can be formed on the bioactive composite structures of the present invention. The topcoat can include any suitable material and can be in any suitable form. It can be amorphous or crystalline, and can include a metal, ceramic, etc. The topcoat can also be porous or solid (continuous).

The topcoat can be deposited using any suitable process. For example, the above-described processes (e.g., electro- and electroless deposition, codeposition or layering) could be used to form the topcoat or another process can be used to form the topcoat. Alternatively, the topcoat could be formed by processes such as, but not limited to, dip coating, spray coating, vapor deposition, etc.

In some embodiments, the topcoat can improve the properties of the bioactive composite structure. For example, the topcoat can include a membrane (e.g., collagen type 4) that is covalently bound to the bioactive composite structure. The topcoat's function can be to induce endothelial attachment to the surface of a bioactive composite structure, while the bioactive material in the bioactive composite structure diffuses from below the topcoat. In another embodiment, a growth factor such as endothelial growth factor (EGF) or vascular endothelial growth factor (VEGF) is present in a topcoat that is on a bioactive composite structure. The growth factor is released from the topcoat to induce endothelial growth while the bioactive composite structure releases an inhibitor of smooth muscle cell growth.

In yet another embodiment of the present invention, the topcoat can improve the radio-opacity of a medical device which includes the bioactive composite structure, while the underlying bioactive composite structure releases molecules to perform another function. For example, drugs can be released from the bioactive composite structure to prevent smooth muscle cell overgrowth, while a topcoat on the bioactive composite structure improves the radio-opacity of the formed medical device. Illustratively, a topcoat comprising, for example and without limitation, nickel, cobalt, Ni—Cr (nickel chromium) and/or gold can be deposited on top of a bioactive composite structure comprising Ni—P to enhance the radio-opacity of a device incorporating the bioactive composite structure. Underneath the topcoat, a smooth muscle cell inhibitor such as sirolimus can be released over a 30-60 day time period from the bioactive composite structure.

The topcoat can also be used to alter the release kinetics of the bioactive material in the underlying bioactive composite structure. For example, an electroless nickel-phosphorous or cobalt-phosphorous coating without bioactive material can serve as a topcoat. This would require the bioactive material to travel through an additional layer of material before entering the surrounding environment, thereby delaying the release of the bioactive material. The release kinetics of the formed medical device can be adjusted in this manner.

In yet another embodiment of the present invention, the topcoat that is on the bioactive composite structure can be a self-assembled monolayer (SAM). The thickness of the self-assembled monolayer can be less than 1 nanometer (i.e., a molecular monolayer) in some embodiments. In one example, a thiol based monolayer can be adsorbed on a nickel matrix of a bioactive composite structure through the thiol functional group and can self-assemble on the nickel matrix. The introduction of the self-assembled monolayer can permit different surface ligands to be used with the bioactive composite structure. That is, various ligands or moieties can be attached to the ends of the molecules in the monolayer that extend away from the bioactive composite structure.

Although medical devices such as stents are discussed in detail, it is understood that embodiments of the invention are not limited to stents or for that matter, to macroscopic devices. For example, embodiments of the invention could be used in any device or material, regardless of size and includes artificial hearts, plates, screws, mems (microelectromechanical systems), and nanoparticle based materials and systems, etc. Further, the substrate can be porous or solid, flexible or rigid, and can have a planar or non-planar surface (e.g., curved).

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed. Moreover, any one or more features of any embodiment of the invention can be combined with any one or more other features of any other embodiment of the invention, without departing from the scope of the invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method comprising:
   creating a template on a surface of a substrate;
   providing a solution comprising metal ions and at least one bioactive material;
   contacting said substrate with said solution;
   forming a bioactive composite structure on portions of said substrate not covered by said template using an electrochemical process selected from a electrodeposition process, an electrocodeposition process, an electroless deposition process and an electroless codeposition process;
   removing said template from said substrate after said formation of said bioactive composite structure thus leaving pores in said structure; and
   loading said at least one bioactive material into said pores thus forming a bioactive composite structure over said substrate.

2. The method according to claim 1, wherein said at least one bioactive material is selected from the group consisting of one or more of rapamycin, paclitaxel and 3-hydroxy-3-methylglutaryl coenzyme A (HMG-CoA) reductase inhibitors.

3. The method according to claim 1, wherein said substrate is a stent.

4. A method comprising:
   providing a first solution comprising metal ions;
   contacting a substrate with said first solution;
   forming a first metal layer on said substrate using an electrochemical process;
   applying at least one bioactive material to said first metal layer such that said at least one bioactive material is contained at least in part with said first metal layer;
   contacting said substrate with said first solution or a second solution;
   forming a second layer metal layer on said substrate using an electrochemical process.

5. The method according to claim 4, wherein said electrochemical process is an electrodeposition process or an electroless deposition process.

6. The method according to claim 4, wherein said first solution, said second solution or said first and said second solution further comprise at least one bioactive material and said first metal layer, said second metal layer or said first and second metal layer further comprise codeposited at least one bioactive material.

7. The method according to claim 4, wherein said bioactive material is selected from the group consisting of rapamycin, paclitaxel and HMG-CoA reductase inhibitors.

8. The method according to claim 4, wherein said substrate is a stent.

* * * * *